United States Patent
Busenhart et al.

(10) Patent No.: US 9,443,058 B2
(45) Date of Patent: Sep. 13, 2016

(54) URINE WORK AREA MANAGER FOR A URINE WORK AREA

(75) Inventors: Mark Busenhart, Cham (CH); Diego Del-Grande, Lucerne (CH); Antonia Voegel, Cham (CH); Urs Vollenweider, Thalwil (CH)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 1045 days.

(21) Appl. No.: 12/841,445

(22) Filed: Jul. 22, 2010

(65) Prior Publication Data

US 2011/0022327 A1 Jan. 27, 2011

(30) Foreign Application Priority Data

Jul. 24, 2009 (EP) .................................... 09166332

(51) Int. Cl.
*G06F 19/00* (2011.01)
*G06K 9/00* (2006.01)
*G01N 21/77* (2006.01)
*G01N 35/00* (2006.01)

(52) U.S. Cl.
CPC ..... *G06F 19/3406* (2013.01); *G01N 35/00603* (2013.01); *G01N 2021/7759* (2013.01); *G06K 9/00127* (2013.01); *Y10T 436/12* (2015.01)

(58) Field of Classification Search
None
See application file for complete search history.

(56) References Cited

U.S. PATENT DOCUMENTS

| | | | |
|---|---|---|---|
| 5,619,428 A | 4/1997 | Lee et al. | |
| 5,675,760 A | 10/1997 | Houwen et al. | |
| 5,851,487 A * | 12/1998 | Katayama et al. | .......... 422/68.1 |
| 5,880,835 A * | 3/1999 | Yamazaki | ............ G01N 15/147 356/336 |
| 6,376,251 B1 | 4/2002 | Braun et al. | |
| 8,008,089 B2 | 8/2011 | Fukuda et al. | |
| 2005/0251347 A1* | 11/2005 | Perona | ............... G06K 9/00134 702/19 |

(Continued)

FOREIGN PATENT DOCUMENTS

CN   1727902 A * 2/2006
EP   0778537 B1   3/2000

(Continued)

OTHER PUBLICATIONS

Machine translation for Sakuraba et al. (JP 06138120, cited by Applicant).*

(Continued)

*Primary Examiner* — Andrew Schechter
*Assistant Examiner* — John Kuan
(74) *Attorney, Agent, or Firm* — Thomas E. Lees, LLC (57) ABSTRACT

A urine work area manager comprises a computing unit and a set of machine executable instructions stored in a memory for execution by the computing unit. The computing unit transfers commands and data between a urine test strip reader and the manager using a first interface, and transfers commands and data between a urine sediment analyzer and the manager using a second interface. In operation, the computing unit instructs the urine test strip reader to analyze a plurality of urine samples, receives a strip analysis result from the urine test strip reader, and generates a first set of instructions for controlling the urine sediment analyzer using the strip analysis result. The computing unit further instructs the urine sediment analyzer to analyze the plurality of urine samples with the first set of instructions and receives a sediment analysis result from the urine sediment analyzer using the second interface.

22 Claims, 6 Drawing Sheets

(56) References Cited

U.S. PATENT DOCUMENTS

| | | | |
|---|---|---|---|
| 2006/0073606 A1 | 4/2006 | Fukuda | |
| 2007/0168225 A1 | 7/2007 | Haider et al. | |
| 2007/0233518 A1 | 10/2007 | Tanaka et al. | |
| 2008/0050278 A1* | 2/2008 | Farina et al. | 422/64 |
| 2008/0310999 A1* | 12/2008 | Yagi | G01N 35/00603 422/65 |
| 2009/0225410 A1* | 9/2009 | Fey | 359/385 |

FOREIGN PATENT DOCUMENTS

| | | |
|---|---|---|
| EP | 1837787 A1 | 9/2007 |
| JP | 2240568 A | 9/1990 |
| JP | 6138120 A | 5/1994 |
| JP | 8315144 A | 11/1996 |
| JP | 2000046835 A | 2/2000 |
| JP | 2005351777 A | 12/2005 |
| JP | 2010054425 A | 3/2010 |
| WO | 2008019695 A2 | 2/2008 |
| WO | 2008097793 A1 | 8/2008 |

OTHER PUBLICATIONS

Geisel, "Automation in urinalysis including autovalidation with SIS-U" Sysmex Xtra Online, vol. N 2, Dec. 2007.*

Mayo et al., "Clinical Laboratory Automated Urinalysis: Comparison Among Automated Microscopy, Flow Cytometry, Two Test Strips Analyzers, and Manual Microscopic Examination of the Urine Sediments" Journal of Clinical Laboratory Analysis 22:262-270 (2008).*

Sysmex; "Product Training UF-1000i, SIS-U", Jan. 2007.

Instrumentation Laboratory; "iQ200 Sprint Product Information, iQ200 Sprint Technical Summary"; Jan. 2007.

77 Elektronika Kft.; "URISED Test Software V3.2 User Manual", Feb. 18, 2008.

77 Elektronika Kft.; "UriSed, Fully Automated Urine Sediment Analyzer, User Manual", Aug. 3, 2007.

77 Elektronika; "UriSed V1.0, Service Manual: UriSed URS-9901-2", May 21, 2007.

English translation-in-part of Japanese Office Action dated Nov. 13, 2012, for corresponding Japanese Patent Application No. 2010-165091, filed Jul. 22, 2010.

Masataka Suzuki, "Introduction of Products, Fully Automated Urine Analyzer US-3100R of Urine Analysis Conveyance System "US-AlpaN"", Sysmex Journal Web, Jun. 23, 2006, vol. 7, No. 2, published on the Internet, see figures 2, 3, 4, 5-1, 5-2, 5-3, 6, 7-1, 7-2 and 7-3.

English translation-in-part of Japanese Office Action dated Aug. 13, 2013, for corresponding Japanese Patent Application No. 2010-165091, filed Jul. 22, 2010.

European Office Action dated Oct. 31, 2012, for corresponding European Patent Application No. 09166332, filed Jul. 24, 2009.

"Urine Test Strip", Wikipedia page, http://en.wikipedia.org/w/index.php?title=Urine_test_strip&oldid=293327586, XP055042128, May 30, 2009.

English translation of Chinese Office Action dated Jan. 13, 2014 for Chinese patent application No. 201010240770.5, filed Jul. 23, 2010.

English translation-in-part of Japanese Office Action dated Mar. 3, 2015, for corresponding Japanese Patent Application No. 2010-165091, filed Jul. 22, 2010; Japan Patent Office.

* cited by examiner

URINE WORK AREA MANAGER FOR A URINE WORK AREA

CROSS REFERENCE TO RELATED APPLICATIONS

The present application claims priority under 35 U.S.C. §119 to European Patent Application EP 09166332.8, filed on Jul. 24, 2009, the entire contents of which are herein incorporated by reference in its entirety.

BACKGROUND

Various aspects of the present invention relate generally to the automated analysis of urine samples, and in particular, to the control of urine chemical analyzers and urine sediments analyzers.

Urine samples are commonly analyzed using a urine test strip reader and/or a urine sediment analyzer. A urine test strip reader is an analyzer that performs a chemical analysis of a urine sample collected onto a test element. An example of a test element is the Combur-Test strip manufactured by Roche Diagnostics Ltd. The chemical analysis can include tests such as measuring the pH of a urine sample. Chemical analysis can also include tests for detecting the presence of specific types of cells or metabolites in the urine sample.

A urine sediment analyzer uses optical means to detect the presence of particulates in a collected urine sample. The urine sediment analyzer may also be able to identify and classify the particulates. For example, a microscope and/or camera can be utilized to examine a urine sample when it flows through a capillary. In another example of a urine sediment analyzer, a centrifuge is used to separate urine sediments from the liquid urine. In the process of centrifuging the urine, the sediments are deposited onto a cuvette bottom which is then examined using a camera and/or microscope. Still further, some urine sediment analyzers are able to identify urine sediments using pattern recognition software. For example, certain urine sediment analyzers are able to distinguish between different cell types such as red blood cells or sperm cells.

BRIEF SUMMARY

According to various aspects of the present invention, a urine work area is provided. According to further aspects of the present invention, a urine work area manager is provided, e.g., for operation in managing functions within a urine work area.

According to various aspects of the present invention, a urine work area manager for controlling a urine test strip reader and a urine sediment analyzer, comprises a computing unit and a set of machine executable instructions stored in a memory for execution by the computing unit. The computing unit transfers commands and data between the urine test strip reader and the urine work area manager using a first interface, and the computing unit transfers commands and data between the urine sediment analyzer and the urine work area manager using a second interface.

In operation, the computing unit executes the set of machine executable instructions to instruct the urine test strip reader using the first interface to analyze a plurality of urine samples, to receive a strip analysis result from the urine test strip reader via the first interface, and to generate a first set of instructions for controlling the urine sediment analyzer using the strip analysis result. The computing unit further executes the set of machine executable instructions to instruct the urine sediment analyzer to analyze the plurality of urine samples with the first set of instructions using the second interface, to receive a sediment analysis result from the urine sediment analyzer using the second interface, and to convey at least one analysis result of the plurality of urine samples.

According to still further aspects of the present invention, a computer program product to manage a urine work area for controlling a urine test strip reader and a urine sediment analyzer, comprises a computer readable storage medium having computer readable program code embodied therewith. The computer readable program code comprises computer readable program code configured to instruct the urine test strip reader to analyze a plurality of urine samples using a first interface to communicate with the urine test strip reader, computer readable program code configured to receive a strip analysis result from the urine test strip reader via the first interface and computer readable program code configured to generate a first set of instructions using the strip analysis result. The computer program product also comprises computer readable program code configured to instruct the urine sediment analyzer, via a second interface, with the first set of instructions to analyze the plurality of urine samples and computer readable program code configured to receive a sediment analysis result from the urine sediment analyzer using the second interface.

DETAILED DESCRIPTION

Like numbered elements in the figures herein, are either identical elements or perform the same function. Elements which have been discussed previously will not necessarily be discussed in later figures if the function is equivalent.

Various aspects of the present invention are directed to a central urine work area manager that controls a urine test strip reader and a urine sediment analyzer. The urine work area manager receives the analysis results of the urine test strip reader and uses the test results to generate control instructions for controlling the urine sediment analyzer. The urine sediment analyzer analyzes the samples, e.g., at least based in part, upon the received control instructions, and produces analysis results. According to further aspects of the present invention, the urine work area manager also receives the analysis results produced by the urine sediment analyzer.

Thus, the urine work area manager is able to compare the results of the urine test strip reader and the urine sediment analyzer. The urine work area manager can decide if the two analysis results agree or if further action should be taken, such as by re-running the tests or by requesting input from an operator. The decision process can be based, for example, upon rules or the decision process can be performed, for example, using an expert system that is part of a computer program product.

Figure 1:
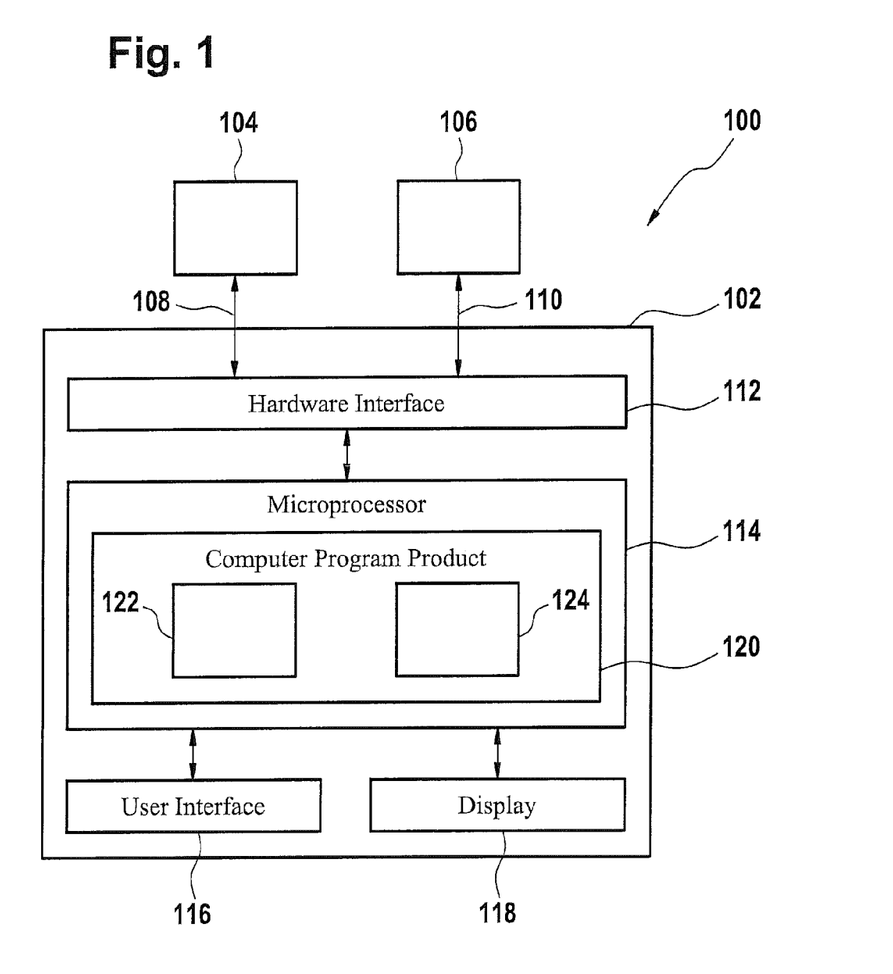
FIG. 1 shows a urine work area, including a urine work area manager having computer program code to control a urine test strip reader and a urine sediment analyzer, according to various aspects of the present invention.

Referring now to the drawings, and in particular, to FIG. 1, an exemplary urine work area 100 is illustrated. The urine work area 100 comprises a urine work area manager 102, a urine test strip reader 104, and a urine sediment analyzer 106. According to aspects of the present invention, the urine work area manager 102 controls the urine test strip reader 104 and the urine sediment analyzer 106 for the testing of urine samples.

A urine test strip reader is defined herein, as an apparatus which performs chemical analysis on urine samples using test elements to determine one or more chemical properties of the urine being tested. This chemical analysis is often performed using strips of chemically impregnated test paper. However, the term test strip reader is used even when the chemical analysis is not performed using a paper test strip. A strip analysis result, as used herein, is any test result or analysis from a urine test strip reader.

A urine sediment analyzer is defined herein, to describe an apparatus which detects the presence of particulates in urine, e.g., using optical means. The term urine sediment analyzer is used even if the particulates do not form sediment during the analysis of the urine. Urine sediment analyzers are able to identify the number and type of different cells or sediments in a urine sample. A sediment analysis result, as used herein, is any test result or analysis from an analyzer which optically detects particles in urine.

The urine work area manager 102 is implemented by a computer system that comprises a computing unit for executing machine executable instructions. The computing unit may be a computer, a microprocessor, an embedded system, a micro-controller or other integrated circuit which is capable of being programmed and/or for executing machine executable instructions.

According to aspects of the present invention, an interface 108, designated herein as a first interface, is provided between the urine work area manager and the urine test strip reader 104. Further, an interface 110, designated herein as a second interface, is provided between the urine work area manager 102 and the urine sediment analyzer 106. The two interfaces 108 and 110 transmit commands and data between the urine work area manager 102 and either the urine test strip reader 104 and the urine sediment analyzer 106.

The first interface 108 is utilized for transferring commands and data between the urine test strip reader 104 and the urine work area manager 102. The first interface 108 may thus be implemented as any sort of interface which is able to transfer information and commands between the urine test strip reader 104 and the urine work area manager 102. Examples of such interfaces are an Ethernet system, universal serial bus (USB) connections, serial port connections, parallel port connections, fire wire connections, optical fiber optic connections, wireless networking connections, and Bluetooth connections. The first interface 108 may also be implemented as software.

The second interface 110 is utilized for transferring commands and data between the urine sediment analyzer 106 and the urine work area manager 102. The second interface 110 may thus be implemented as any sort of interface which is able to transfer information and commands between the urine sediment analyzer 106 and the urine work area manager 102. Examples of such interfaces are similar, and thus analogous, to the exemplary interfaces identified with reference to the first interface 108. The second interface 110 may be identical to the first interface 108, or the first interface 108 and the second interface 110 may be different, e.g., physically implemented as separate interfaces, which could be different types of interface implementations.

The illustrated urine work area manager 102 also comprises a hardware interface 112, a microprocessor 114, a user interface 116 and a display 118. The hardware interface 112 couples the microprocessor 114 to the first interface 108 and the second interface 110, such that the urine work area manager 102 can transmit data to, and receive data from, the urine test strip reader 104 and the urine sediment analyzer 106. The user interface 116 receives input from a user or operator. User interaction is described in greater detail herein. The display 118 is utilized by the urine work area manager 102 to display information about the urine test strip reader analysis results and the urine sediment analyzer results and also to present an operator with choices to select when appropriate, based upon the functioning of the urine work area manager 102.

The urine work area manager 102 also comprises a computer program product 120 for execution by the microprocessor 114. The computer program product comprises machine executable instructions 122 for performing machine executable processes according to various aspects of the present invention, as will be described in greater detail herein. The computer program product 120 may also comprise an expert system 124. The expert system 124 receives analysis results of the urine test strip reader 104 and/or the urine sediment analyzer 106. The expert system 124 can be used to perform such tasks as deciding if a sample should be rerun, deciding if a needle of the urine test strip reader 104 should be cleaned, deciding if individual urine samples should be put into a sub-group of urine samples that will be reanalyzed, and also for deciding what analysis should be repeated, if necessary, for a particular urine sample.

According to various aspects of the present invention, the computer program product 120 may be implemented as a set of machine executable instructions, which are essentially machine executable program(s) which can be stored and then executed by the computing unit of the urine work area manager 102, e.g., the microprocessor 114. The machine executable instructions may be stored externally to the computing unit and loaded later or the machine executable instructions may be stored on a hard drive system of the urine work area manager 102. The machine executable instructions instruct the urine test strip reader 104 via the first interface 108 to analyze a plurality of urine samples. The machine executable instructions further receive a strip analysis results from the urine test strip reader, e.g., using the first interface 108.

The results of the urine test strip analyzer 104 can be used to control how the urine sediment analyzer 106 analyzes the plurality of urine samples. As an illustrative example, the machine executable instructions receive a strip analysis result from the urine test strip reader 104 via the first interface 108. The machine executable instructions further generate a first set of instructions using the strip analysis result. By using the strip analysis result, it is meant that data comprising the strip analysis result is used to determine what the first set of instructions are. The instructions could be based on the data comprising the strip analysis result or the instructions could be based upon the result of a calculation or an algorithm that uses the data as input. The machine executable instructions communicate with the urine sediment analyzer 106 across the second interface 110, to instruct the urine sediment analyzer 106 using the first set of instructions, to analyze a plurality of urine samples. Thus, the results of the urine test strip reader 104 are used to generate instructions for the urine sediment analyzer 106. The machine executable instructions further receive a sediment analysis result from the urine sediment analyzer 106 using the second interface 110.

Thus, decisions can be made before analyzing the urine sample with the urine sediment analyzer 106 which are not conventionally possible or easy, such as determining that the urine needs to be diluted before being analyzed by the urine sediment analyzer 106. For example, urine sediment analyzers 106 typically use pattern recognition software to examine images to identify the different types of cells contained in the image. If the images are crowded with too many cells, then the pattern recognition software will not be able to recognize and identify the type and number of cells or sediments in the urine sample. In this particular example the urine test strip reader 104 can be used to project if the urine sediment analyzer 106 should dilute the urine sample before performing the operation. This results in higher quality and more reliable results from the urine sediment analyzer.

As an illustrative example, a first set of instructions is generated by the urine work area manager 102, using the strip analysis result by checking the strip analysis result to determine if each of the plurality of urine samples meets a first predetermined condition. For example, the first set of instructions may be generated using the strip analysis result by generating instructions for the urine sediment analyzer 106 to dilute each urine sample that meets the first predetermined condition. Thus, chemical analysis by the urine test strip reader 104 can be used to determine if the urine should be diluted before it is analyzed by the urine sediment analyzer 106. This can be used to avoid a situation where the image is too crowded and the pattern recognition software of the urine sediment analyzer therefore does not function properly because the image is too crowded.

The urine test strip reader 104 and the urine sediment analyzer 106 work using different principles. Thus, there may be circumstances where the two tests do not agree. In some cases the urine test strip reader 104 and the urine sediment analyzer 106 may disagree because there is an error in performing one of the tests or there may be a difference due to the age of the urine sample. For example, a urine test strip reader 104 may detect older erythrocytes in a urine sample, whereas with the urine sediment analyzer 106, the erythrocytes may be broken apart and not be able to be identified by pattern recognition software.

However, according to further aspects of the present invention, the set of machine executable instructions can include code to identify a sub-group of a plurality of urine samples for which the strip analysis results and the sediment analysis results disagree. The determination may be identified, for example, by detecting disagreements above a predetermined threshold. Hence, the urine samples in the sub-group are urine samples which had ambiguous test results or likely have test results with errors. The set of machine executable instructions can thus further instruct the urine test strip analyzer 104 and/or the urine sediment analyzer 106 to reanalyze urine samples in the sub-group.

As noted above, the urine work area manager 102 may comprise an expert system. According to aspects of the present invention, the sub-group is identified using the expert system. In this regard, determining when to reanalyze the urine samples may involve complex relationships that cannot be identified with a simple formula. The expert system however, can compare the results of the urine test strip reader 104 and the urine sediment analyzer 106, e.g., using a rule based system.

According to further aspects of the present invention, the urine work area manager 102 comprises a display for displaying images. The machine executable instructions display at least one image acquired by the sediment analyzer 106 for each urine sample in a corresponding sub-group. The machine executable instructions further receive input from an operator for each urine sample in the sub-group indicating if the urine sample should remain in the sub-group or should be removed from the sub-group. The machine executable instructions remove each user identified urine sample from the sub-group before instructing the urine sediment analyzer to reanalyze the urine samples in the sub-group. Thus, an operator may be prompted to select if a urine sample should be reanalyzed or not. This results in a saving of time, because the samples which should be reviewed by an operator are displayed automatically for an operator to review.

According to still further aspects of the present invention, the urine work area manager 102 utilizes machine executable instructions to receive a series of image analysis results from the urine sediment analyzer 106, e.g., as each image analysis result is acquired for each of the plurality of urine samples. An image analysis result is defined herein, as information which characterizes the urine sediments that a urine sediment analyzer 106 identifies in a urine sample. For instance, a urine sediment analyzer may use a centrifuge to deposit sediments on a substrate which is then subsequently imaged using an imaging system.

According to aspects of the present invention, the urine sediment analyzer 106 makes images at a variety of different places on the substrate. Image analysis results are generated for each image that is taken by the urine sediment analyzer 106. The machine executable instructions stop the acquisition of further image analysis results if all image analysis results are within a statistical threshold. It takes time for the urine sediment analyzer 106 to acquire images and analyze them. If the image analysis results of all the images in the series have a very similar result, then there may not be a need to analyze further images. This reduces the analysis time. In an exemplary implementation, a predetermined/set number of image analysis results, e.g., images, is established. The urine work area manager 102 receives the set number of image analysis results and then determines if further image analysis results should be acquired by the urine sediment analyzer 106.

According to still further aspects of the present invention, the strip analysis result is used in the determination of the statistical threshold. The urine test strip reader 104 and the urine sediment analyzer 106 are often able to identify similar types of cells or sediments in the urine. If the series of image analysis results of the urine sediment analyzer 106 are within a statistical threshold and they agree with the results of the urine test strip reader 104, then the confidence that the analysis result is correct is much higher. This leads to a faster analysis that has a high degree of confidence of a correct reading. If the series of image analysis results agree with each other within a high degree of statistical confidence, but the series of image analysis results still disagree with the urine test strip reader results, the system may continue acquiring more image analysis results so that a better decision can be made if the urine sample should be reanalyzed or needs to be examined by an operator.

According to still further aspects of the present invention, the machine executable instructions executed by the urine work area manager 102 can be executed to analyze the urine sample in research mode. The machine executable instructions instruct the urine sediment analyzer 106 to acquire a series of image analysis results for the urine sample using a first predetermined number of images. Research mode is defined herein as being a mode where a detailed analysis of the urine is made. When such a mode is selected, a larger number of images than is normally used during normal operation are taken and analyzed to obtain statistics on the urine sediments.

According to still further aspects of the present invention, the machine executable instructions further comprise code executable to display a summary of the strip analysis result(s) and a sediment analysis result(s), e.g., using the display 118. Such machine executable instructions receive an input from the operator, e.g., via the user interface 112, indicating approval or disapproval of the strip analysis result and the sediment analysis result for each urine sample. The machine executable instructions may also and/or alternatively, enable a user to edit and/or append a comment to the results. It is understood that the results refers to the strip analysis result and/or the sediment analysis result.

Thus, the results of the urine test strip reader 104 and the urine sediment analyzer 106 are summarized in the form on the display which an operator can either approve or disapprove of. The display can be utilized to output a summary of the results of the urine test strip reader 104 and the urine sediment analyzer 106. In particular, a comparison of the urine test strip reader 104 and the urine sediment analyzer 106 can be displayed when they give contradictory results. Accordingly, for example, if the urine analysis results are not approved, they can be placed into a sub-group of samples for which the results were questionable. Samples in the sub-group can then be re-run and reanalyzed by the urine test strip reader 104 and/or the urine sediment analyzer 106. Samples in the sub-group can also be marked to be subject to a user review of the results.

The urine test strip reader 104 may comprise a needle for dispensing urine during operation. In this regard, according to aspects of the present invention, machine executable instructions may further comprise code to instruct the urine test strip reader 104 to re-analyze urine samples in the sub-group and to wash its needle. Communication may be carried out, for example, across the first interface 108. For instance, in certain operations, the results of the urine test strip reader may be questionable and it may be necessary to clean the needle more thoroughly than it was when the test results were originally taken.

According to still further aspects of the present invention, the machine executable instructions graphically display which of the plurality of urine samples are a member of the sub-group before instructing the urine sediment analyzer 106 to re-analyze the urine samples that are a member of the sub-group. Those urine samples which need to be reanalyzed are clearly displayed on the display 118. This allows an operator to see which samples will be rerun and which ones will not be rerun. In an illustrative example, the operator is able to select urine samples to become a member of the sub-group or de-select urine samples to remove them from the sub-group. The display 118 can display the samples graphically such that a operator can easily tell which urine samples are a member of the sub-group and which are not. This allows the operator to be able to manually remove or sort samples which are, or are not, members of the sub-group. Thus, for example, the operator can look at the display 118 and be able to easily remove samples from the sub-group or add samples which are currently not a member of the sub-group.

According to yet still further aspects of the present invention, the urine work area manager 102 receives a sediment analysis result which comprises at least two images of different portions of the same sample. In operation, the machine executable instructions graphically display, e.g., on the display 118, the relative numbers of different types of sediments in each of the at least two images. Thus, an operator can see the results of the analysis of the different images. This allows an operator to observe if the relative numbers of different types of particulates in the urine are consistent from image to image. If the results are consistent from image to image, then the operator will have more confidence in the result. By way of illustration, in an exemplary implementation, a selector may be provided, which allows an operator to select images based on the relative numbers of different types of particulates. The selector may be implemented either in hardware or in software. If one or several images have results which differ from the others, the operator would then be easily able to identify and review the images that were used to generate these results.

According to further aspects of the present invention, the machine executable instructions further comprise graphically displaying a summary of the strip analysis result and the sediment analysis result. The strip analysis result comprises at least one chemical analysis and the sediment analysis identifies the quantity of at least one type of particulate. The summary shows the at least one chemical analysis and the quantity of at least one type of particulate, e.g., using normalized graphs. For instance, the display of the strip analysis results and the sediment analysis result can be normalized such that the normalization allows the easy identification of normal and abnormal test results in a way that allows the operator to see graphically, how far the test result varies from a normal result. The graphs may be displayed with fields of all the same scale length. The graphs may also be scaled to show the relevant scale for the measurements. For instance, the pH scale may start at 5 and may end at 9. The display 118 of the urine work area manager 102 may be, but is not limited to, being a computer monitor or display screen.

According to yet further aspects of the present invention, the urine work area manager 102 further comprises a microscope selector (not shown in FIG. 1). The microscope selector may be, but is not limited to, a selection on a graphical user interface or it may be a button on a control panel. The machine executable instructions include for example, instructions for activating a microscope control interface when the microscope selector is selected. The control interface may be, but is not limited to being, a control panel implemented in a graphical user interface or a set of controls on a control panel such as push buttons and a joystick. The microscope control interface receives user input and generates microscope control instructions which are sent to the urine sediment analyzer 106 via the second interface 110. These control instructions in particular, comprise the choice of field of view and focal settings. The display 118 is utilized to display microscope images received via the second interface 110 from the sediment analyzer 106. Thus, an operator can manually inspect the urine samples without the need for an additional microscope.

The machine executable instructions may also output a signal. As a few illustrative examples, the machine executable instructions may output a signal whenever any one of the following occurs: the urine sediment analysis result contains more than a second predetermined number of unclassified particles, the urine sediment analysis result contains more than a third predetermined number of particles, the urine work area manager 102 is being operated in a research mode. If the sediment analysis result contains more than a second predetermined number of unclassified particles, it may mean that there are too many unclassified particles to give an accurate result. If the sediment analysis result contains more than a third predetermined number of particles, it may mean that there are too many particles for the pattern recognition software to function properly. When there are too many particles for the pattern recognition software to function properly, this is known as a crowded condition. Thus, an operator is alerted of a situation in which it would be beneficial to examine images from the sediment analyzer 106 manually. The signal could be a lighted indicator, it could be a sound, or it could be a message box or dialogue box on a graphical user interface. However, as an illustrative example, an alert is displayed on the regular display 118 by color coding or flagging.

Accordingly, as used herein, a urine work area manager 102 is a computational system such as a computer, computer system, or embedded system which provides central control and analysis of a urine test strip reader 104 and a urine sediment analyzer 106. The urine work area manager 102 may be, but is not limited to being, a standalone computer that is interfaced with the urine test strip reader 104 and/or the urine sediment analyzer 106. The urine work area manager 102 may alternatively be implemented as a computer or controller integrated into the urine test strip reader 104, a computer or controller integrated into the urine sediment analyzer 106, or a computer or controller integrated into a combined urine test strip reader 104 and urine sediment analyzer 106. For instance, in a non-limiting exemplary implementation, the urine work area manager 102 is located within the same housing as the urine sediment analyzer 106. The urine work area manager 102 and the urine sediment analyzer 106 are further operated using the same computation unit. Thus, the second interface 110 is implemented in software to reduce the number of computational units necessary.

As used herein the term re-analyze means to re-run a sample, to perform a new test or set of test on a sample, or to examine a sample using microscopy. As used herein, the term instructing means providing a set of machine readable instructions or signals that instruct a machine, apparatus, or computational device to perform a specific task.

Figure 2:
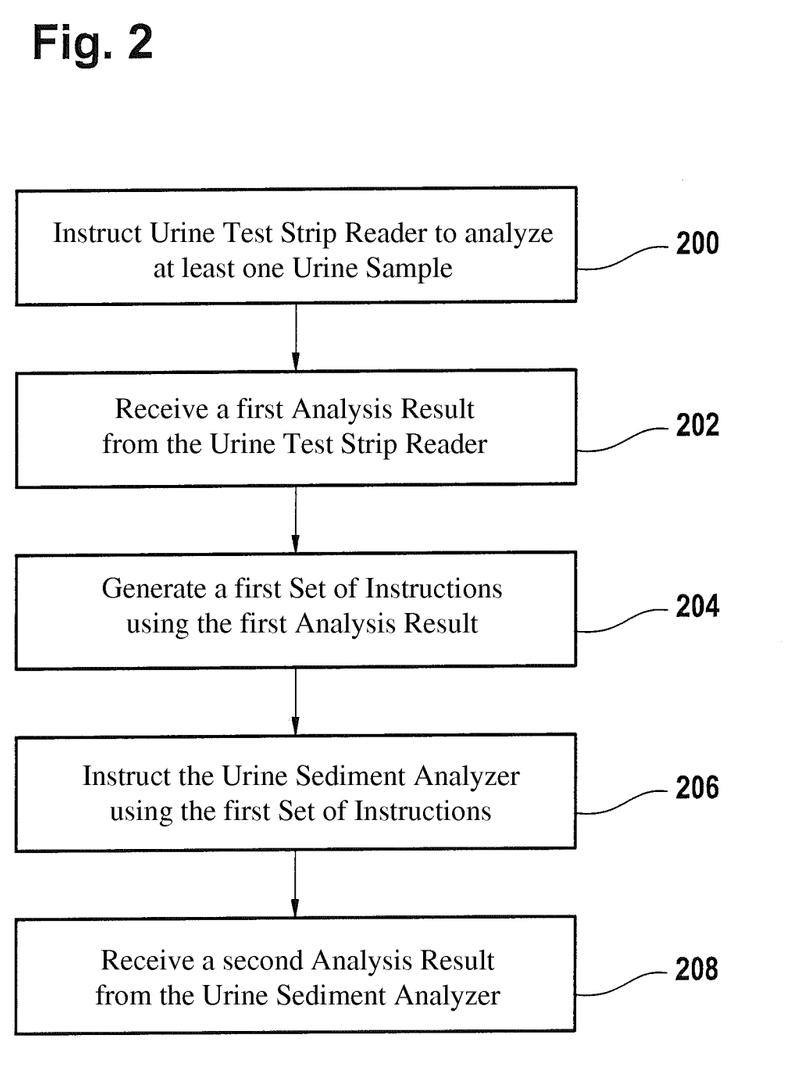
FIG. 2 is a block diagram of a method for controlling a urine strip reader and a urine sediment analyzer that can be implemented using machine executable code, according to various aspects of the present invention.

FIG. 2 shows a method that can be performed using, for example, the machine executable instructions 122 of computer program product 120, according to various aspects of the present invention. The urine test strip reader is instructed to analyze at least one urine sample at 200. A strip analysis result is received from the urine test strip reader at 202. A first set of instructions is generated using the strip analysis result at 204. The urine sediment analyzer is instructed to analyze the urine sample(s) using the first set of instructions at 206. Thus, the first set of instructions is generated using the strip analysis result. Accordingly, the results of the urine test strip reader are used to control how the urine sediment analyzer analyzes the urine sample(s). A sediment analysis result is received from the sediment analyzer at 208. The output of at least one analysis is conveyed to an output device, e.g., the display 118, a printer, etc.

Figure 3:
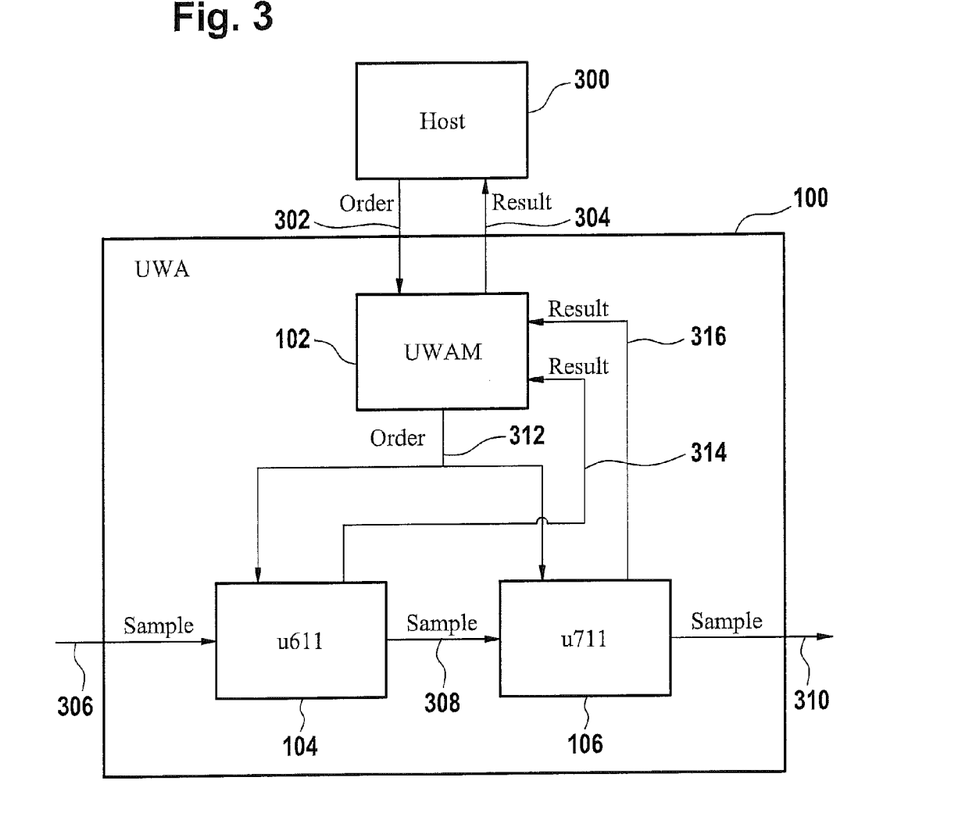
FIG. 3 shows a urine work area according to various aspects of the present invention.

FIG. 3 shows a host 300, such as a computer that sends instructions to a urine work area 100 via a network interface 302 for controlling the urine work area. After sending an order to the urine work area 100, the host 300 receives the result of the order 304 via the network interface. As noted above with regard to FIG. 1, the urine work area 100 comprises a urine work area manager 102 (also designated as a Urine Work Area Manager (UWAM) in FIG. 3), a urine test strip reader 104 and a urine sediment analyzer 106.

However, as illustrated, the urine work area manager 102 communicates over an interface 312 for controlling the urine test strip reader 104 and the urine sediment analyzer 106. The urine test strip reader 104 communicates results back to the urine work area manager 102. In this regard, the results can be communicated back to the urine work area manager 102 over the interface 312 or a different interface, such as interface 314 as illustrated. Similarly the urine sediment analyzer 106 communicates analysis results back to the urine work area manager 102 over the interface 312 or a different interface, such as the interface 316 as illustrated.

FIG. 3 also shows the flow of urine samples through the urine work area 100. At position 306, the urine sample is shown before it is analyzed by the urine test strip reader 104. At position 308, the urine sample has been analyzed by the urine test strip reader 104. The result of the urine test strip analysis is then communicated back to the urine work area manager 102, e.g., using interface 314. The urine work area manager 102 may send instructions to the urine sediment analyzer 106 on how to process the urine sample. When the urine sample is in position 310 the urine sample has been analyzed by both the urine test strip reader 104 and the urine sediment analyzer 106.

In the illustrative exemplary configuration of FIG. 3, the urine work area manager 102 may be responsible for performing one or more of the following tasks:

downloading an order from the host 300 to analyze a urine sample;

forwarding the order to analyze the urine sample to the urine test strip reader 104 (also designated u611 in FIG. 3) or the urine sediment analyzer 106 (also designated u711 in FIG. 3);

combining the individual results of the urine test strip reader and the urine sediment analyzer into a combined result for every sample;

validating the combined result of the urine sediment analyzer and the urine test strip reader;

re-running the resultant test strip analysis and/or urine sediment analysis if necessary; and documenting combined results. The results may be uploaded to the host.

In some cases a sample must be manually reloaded into the system when re-running the resultant test strip analysis and/or urine sediment analysis, depending upon the specific implementation.

The urine work area manager 102 may aid the operator in interpreting the results from the test strip analysis and/or urine sediment analysis. This may be accomplished by:

flagging results which indicate critical values or test results; and implementing intelligent flagging, which could include technical validation or an automated flagging based on an expert system.

According to various aspects of the present invention, the urine work area manager 102 may aid the operator in interpreting the results from the test strip analysis and/or urine sediment analysis using predetermined rules which may be configurable by the operator. For example, a rule could set a flag for the following disagreements between the urine test strip and urine chemical analysis:

| Urine test strip analysis | Urine Sediment analysis | Flag |
|---|---|---|
| Erythrocytes pos. | Erythrocytes neg. | √ |
| Erythrocytes neg. | Erythrocytes highly pos. | √ |
| Leukocytes pos. | Leukocytes neg. | √ |
| Leukocytes neg. | Leukocytes highly pos. | √ |
| Nitrite pos. | Bacteria neg. | √ |
| Protein neg. | Pathological casts pos. and/or hyaline casts pos. | √ |
| Protein neg. | Sperm pos. | √ |
| Protein strongly pos. | Sperm neg. | √ |

According to further aspects of the present invention, the urine work area manager 102 may aid the operator in interpreting the results from the test strip analysis and/or urine sediment analysis through:
  visualizing of parameter samples, for example, by providing different graphical representations such as bar charts, to better depict and identify different pathologies;
  training the system, such as by correlating results of diagnosis with the results of the urine analysis for training an expert system; and
  facilitating manual validation by the operator, for example, by providing post processing of samples with "unclassified" particles.

The ability of the urine work area manager 102 to aid the operator in interpreting the results from the test strip analysis and/or urine sediment analysis offers intuitive validation of the urine analysis results.

As noted in greater detail above, to better identify particles in the urine sediment, the urine can sometimes be diluted. A pre-thinning of the urine can be based on the result of the urine strip analysis or other test results. The following criteria are presented by way of illustration, and not by way of limitation, to describe criteria that can be used to order a thinning of the urine:
  a) Based on the urine strip analysis:
    1. A thinning of the urine is ordered whenever the following results are measured:
      Leu: 3+(Range 500/μl);
      Ery/Hb: 4+(Range 150/μl);
      Nitrite positive, e.g., highly positive according to remission values;
      Combinations of the previous three levels, for example when Ery 3+(Range 50/μl) and Leu 2+(Range 100/μl)). Samples which need dilution could also be determined using an expert system which considers a combination of criteria.
    2. Physical Measuring Cell results (PMC)
      The urine is cloudy;
      Color of the urine.
  b) Based on the results of the urine sediment analyzer:
    crowded samples (for example an abundance of epithelial cells);
    in special cases specified by an operator.

Urine sediment analyzers typically analyze a predetermined number of images to determine the composition of the urine sample. For example, a urine sediment analyzer can be instructed to collect 5, 10, 15 or 20 images for analysis. In many cases a sample of 15 different images is necessary to ensure that accurate results are obtained.

However, according to various aspects of the present invention, a fast screening mode is utilized to analyze the results of the urine sediment analyzer 106. As such, the urine sediment analyzer 106 of the urine work area 100 described more fully herein, is able to reduce the number of images necessary for analysis. This reduces the bottleneck caused by the acquisition and analysis of the images in the analysis of urine samples. For example, if the image is crowded and good results are not obtained in the first 5 images, the test can be terminated. If a predetermined number of results agree with each other, the test results can be given with a smaller number of frames. This is particularly true if the results agree with results obtained from the urine test strip reader 104.

Figure 4:
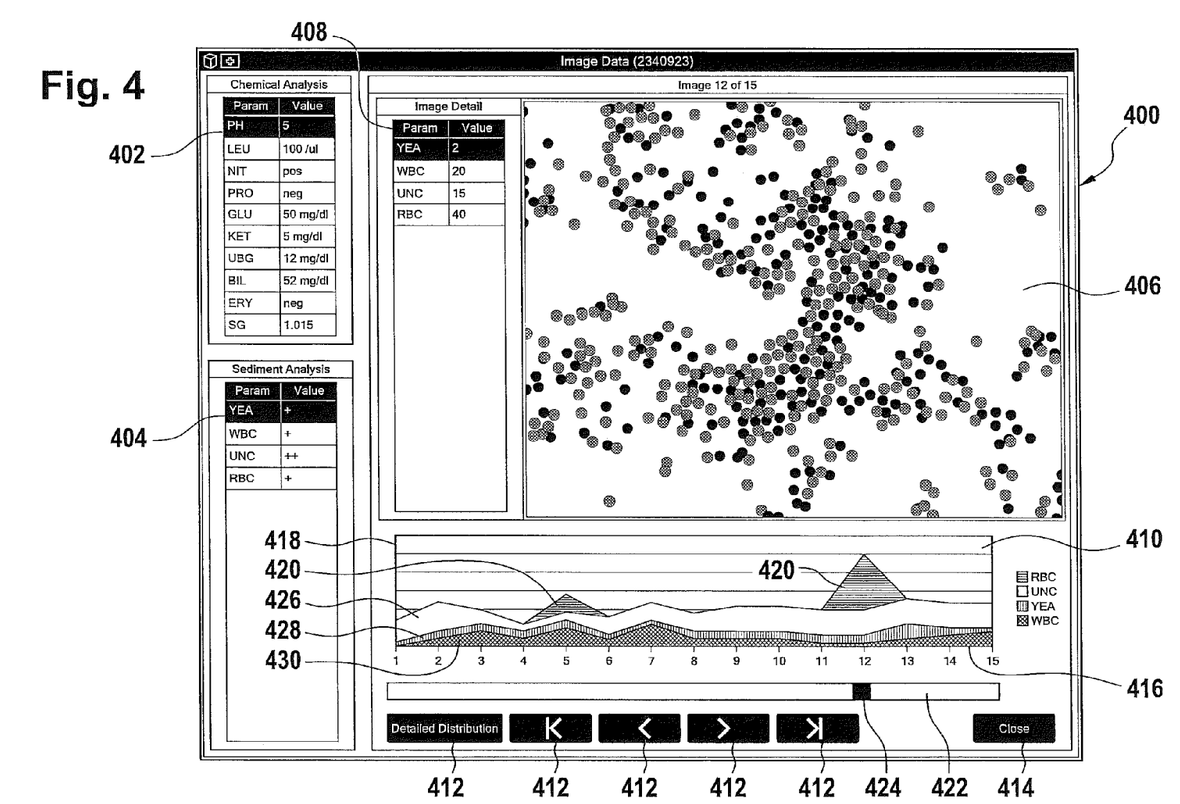
FIG. 4 shows an example of a graphical display of urine analysis results, according to various aspects of the present invention.

FIG. 4 shows an example of a graphical display 400 of urine analysis results according to various aspects of the present invention. RBC is an abbreviation for red blood cell. ERY is an abbreviation for erythrocytes. WBC is an abbreviation for white blood cell. LEU is an abbreviation for leukocytes. BAC is an abbreviation for bacteria. NEC is an abbreviation for non-squamous epithelial cells. PAT is an abbreviation for pathological casts. PRO is an abbreviation for protein. GLU is an abbreviation for glucose. KET is an abbreviation for ketone. UBG is an abbreviation for urobilinogen. BIL is an abbreviation for bilirubine. SG is an abbreviation for specific gravity. MUC is an abbreviation for mucus. YEA is an abbreviation for yeast. UNC is an abbreviation for unclassified. CRY is an abbreviation for crystals.

Region 402 shows a summary of the test strip or chemical analysis of the urine, e.g., from the urine test strip reader 104. Region 404 shows a summary of the results of the urine sediment analyzer 106 for a series of images. Region 406 shows a currently selected image that has been acquired by the urine sediment analyzer. Navigation through the images acquired by the urine sediment analyzer 106 is discussed below. Region 408 shows a summary of the urine sediment analysis for the image displayed in region 406. Region 410 shows a graphical summary of the urine sediment analysis for each of a series of 15 images. There are a collection of clickable buttons which are a user interface 412 for controlling the display of the urine sediment analysis results. Different images can be selected or they can be examined in more detail. Button 414 is a clickable user interface for closing the graphical display of the urine analysis. Region 410 shows a graphical summary which allows an operator to see a summary of the contents of each of the images all displayed together.

In region 410, there is a horizontal axis 416 for which each number represents an image that was analyzed by the urine sediment analyzer 106. The vertical axis 418 shows the relative quantities of various particulates in each of the images. In this particular example it can be seen that two of the images, images 5 and 12 have large quantities of red blood cells 420. There is a selector 422 below the horizontal axis 416. The operator can click below the image number to choose to which image 406 to display. The button 424 in the selector 422 shows that the current image is image number 12. In region 410 the quantities of unclassified particles (UNC) 426, yeast 428, and white blood cells 430 are also shown.

The region 410 allows an operator to quickly see if the various images used during the urine sediment analysis show consistent results or if several images should be examined in more detail. If all the various types of sediments are very constant for the first few images, then the analysis can be shortened as was described for the fast screening mode. In the example that was shown here, several image showed relatively large concentrations of red blood cells, which can indicate a serious health problem.

Automated urine sediment analyzers have the disadvantage that if the concentration of urine sediments is too large then the image becomes "crowded". That is, too many different sediments are overlapping for the pattern recognition software to function properly. If this is the case, then the urine sample must be diluted and analyzed using the urine sediment analyzer again. However, according to various aspects of the present invention, the occurrence of such a situation can be detected by the strip analysis result and dilution can be made automatically in advance of the urine sediment analysis. According to still further aspects of the present invention, microscope functionality can be implemented in the urine sediment analyzer 106 using this same optical system used to acquire the image 406, where the user manually operates the microscope, e.g., by manipulating the microscope via the input keys of the sediment analyzer 106. According to various aspects of the present invention, the microscope may also be operated via a dedicated hardware control. In this regard, the user can set parameters of the microscope such as, but not limited to, the view field and focus. Using this microscope interface, fully automated results that indicate a problem can be investigated in more detail. For instance, a user can manually investigate automated results, such as where the results were not plausible, there were unclassified particulates, or the results were too crowded. Using this microscope system the operator can examine the images and determine the reason for the anomalous or suspicions results from the urine sediment analyzer.

The above described aspects of the present invention enable a more efficient workflow than when the urine sample is analyzed later after the urine sediment analysis is finished. Using the microscope functionality of the urine sediment analyzer 106, the analysis of microscopic images from the urine sample can be integrated into the normal work flow. Essentially the urine sediment analyzer 106 can be operated in a microscope mode as described above. Microscope mode is defined herein, as a mode of operation of a urine sediment analyzer 106 in which the optical system of the urine sediment analyzer 106 is used as a manually controlled microscope.

According to aspects of the present invention, the operator inspecting the images does not need to be present in the laboratory. For instance, a physician or an expert operator could examine the urine sample results remotely. After examination the operator can decide if the sample should be re-run or can add notations to the test result explaining the results.

The workflow of using the microscope mode is the same as for a normal measurement, except that after checking the automated results, a user decides to manually repeat the measurement using the urine sediment analyzer 106. This can be performed with the same cuvette which already has been used for automated sediment analysis or a new cuvette may be prepared from the same sample.

An example of a possible work flow using the above-described microscope is set forth below:
  a decision is made to re-run the urine sediment analyzer 106 with manual investigation. The sample number and test parameters, which are to be measured again manually (sediment parameters) are defined;
  the urine samples that are to be measure again are placed into the input buffer of the urine sediment analyzer;
  the sample ID and the Rack ID is checked;
  the urine sediment analyzer 106 automatically changes into microscope mode as soon as the sample has been pipetted into the cuvette and has been centrifuged so as to be ready for the manual analysis;
  in manual mode, the operator can freely choose the position of the image, focus the images, and determine the number of images of the sample taken (the number of images in principle can be arbitrary);
  the manually taken pictures can be evaluated manually by the operator and/or the image processing system or the urine sediment analyzer 106 can analyze the image and return a list of particulate types and numbers;
  any manually or automatically obtained results are attached to the sample's records and test results. A physician may have access to all of the test results that were measured by the system, and the physician would have knowledge that an operator had performed a manual investigation in microscope mode.

Possible reasons why the microscope mode would be used include: suspicious pathology, a very infrequent type of particulate, the concentration of particulates is so high that the image is crowed that it is not possible to determine cell concentrations, and no result from the image processing can be obtained. An example of an infrequent type of particulate is a pathological cylinder, which is a cylindrical agglomeration of cells indicating renal disease.

Figure 5:
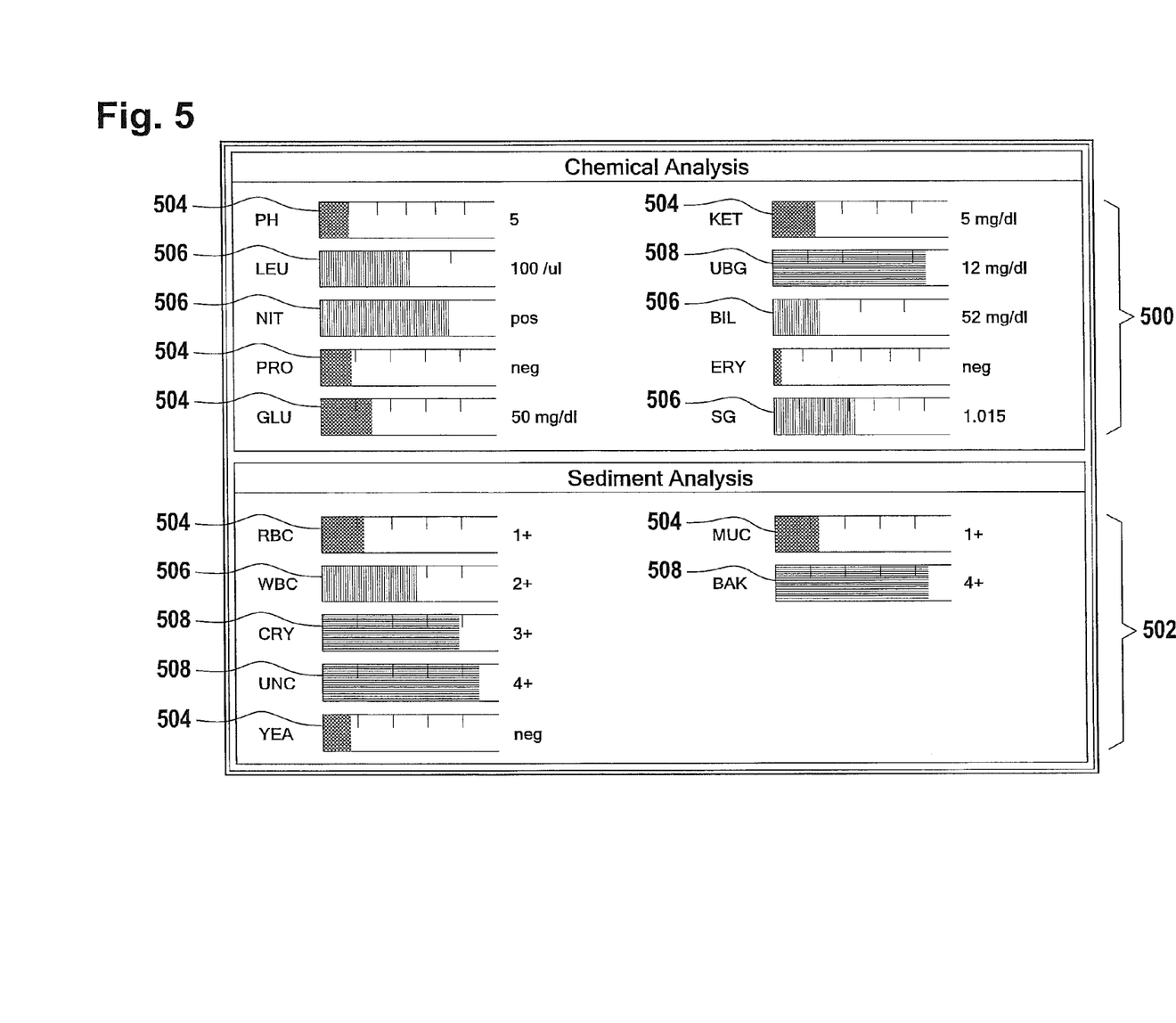
FIG. 5 shows a further example of a graphical display of urine analysis results, according to various aspects of the present invention.

FIG. 5 shows an example of a result overview for the urine strip analysis and the urine sediment analysis that is displayed graphically. FIG. 5 shows a summary of the chemical or urine test strip analysis 500 and a summary of the urine sediment analysis 502. The data in this result overview can be color coded or marked so that an operator will note results which are critical or indicate a positive result. Results in this figure labeled 504 are considered uncritical. Results labeled 506 require attention because they may indicate a health problem or they may not indicate a health problem. Results labeled 508 are considered to be positive results. In this case the result of the chemical analysis and the sediment analysis is clear.

The results of the urine test strip analysis or the urine sediment analysis are displayed graphically in FIG. 5. In the bar graphs there are many possibilities for displaying information.

For example, the color can be used to code the results. For example green could mean that the results is not critical, yellow could mean that the results should be examined by an operator or physician, and red could mean that the result is positive. For example, a large number of blood cells in the urine could trigger a red color coded result. The color coding and the thresholds of results may be specified by an operator or user of the system.

The scale of the bar graph can also be used to indicate important information. For instance the scaling can be normalized so that an operator can see how an analysis by the urine test strip analyzer 104 or the urine sediment analyzer 106 compares to a threshold. Thresholds can be chosen by an operator or are set as defaults in the system according, for example, to medical relevance. Colors can also chosen by the operator or set as defaults in the system and may be displayed according to the measurement results.

According to yet further aspects of the present invention, the urine work area manager 102 comprises a network interface. The machine executable code receives a command via the network interface to analyze the plurality of urine samples. Thus, a remote computer system can be used to control the urine work area manager.

Figure 6:
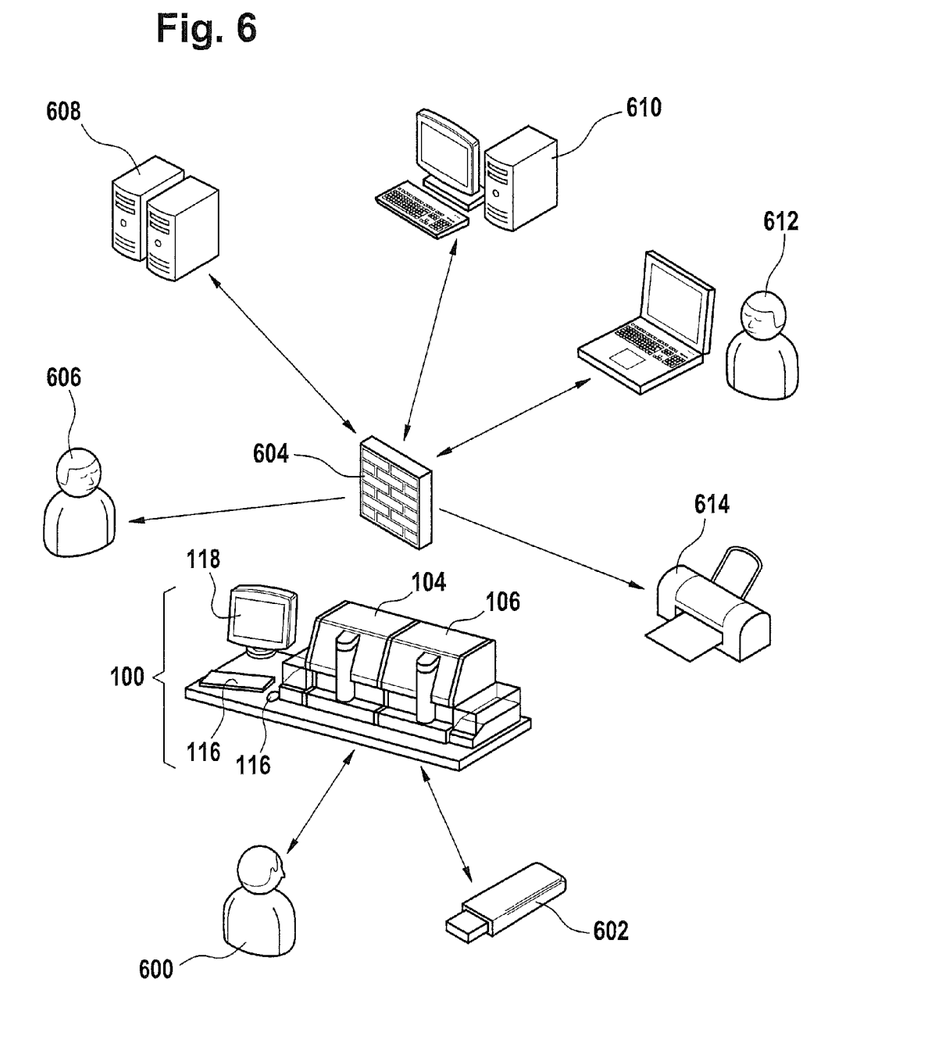
FIG. 6 illustrates the integration of a urine work area into a computer network, according to various aspects of the present invention.

FIG. 6 illustrates the integration of a urine work area 100 into a computer network. There is a urine work area 100 shown. The urine work area 100 has a urine test strip reader 104 and a urine sediment analyzer 106 that are shown connected together. The urine work area also has a display 118 for displaying data and graphical information. Also shown are a keyboard and a mouse which function as a user interface 116. The urine work area manager 102 is not shown, but may be an independent computer or may be integrated into the urine test strip reader 104 or the urine sediment analyzer 106. Local user 600 is an operator who can operate the urine work area 100 using the display 118 and user interface 116. Test results may be stored on an external storage device 602 such as a USB drive.

The urine work area manager is connected to a firewall 604 to protect the urine work area manager. The firewall 604 may be implemented as software or may be a separate hardware firewall. Through a computer network, a variety of systems and people may retrieve information from and send commands to the urine work area 100.

Item 606 is a remote user of the urine work area 100. The remote user 606 may be a physician who sends orders or instructions to the urine work area manager 100. For instance, the remote user 606 may send an order to analyze a group of urine samples, the remote user 606 may select certain urine sample to be analyzed in research mode, or the remote user 606 may even use the optical camera of the urine sediment analyzer 106 in microscope mode remotely. This allows a busy physician to examine a urine sample from the convenience of his or her office without the necessity of going to the laboratory.

Item 608 is a connection to a healthcare information technology environment. Item 608 could for instance, be implemented as a lab information system, which is an information system that receives, processes, and stores information generated by medical laboratory processes. Item 608 could also comprise a hospital information system or clinical information system, which manages the administrative, financial, and clinical aspects of a hospital. Connecting with a healthcare information technology environment allows better workflow in the laboratory and allows the test results to be better integrated into the patient's medical records.

Item 610 is a connection to a factory. This allows, for example, the manufacturer of the urine work area 100 to monitor and possibly even upgrade the urine work area 100. Item 612 represents a connection to a service representative. This is advantageous, because a service representative 612 can perform a quick analysis of the system in the case of problems without traveling to the hospital. This reduces service costs and reduces the down time of the urine work area 100. A printer 614, for printing analysis results, can also be connected to the system, e.g., by connecting to the firewall 604, as illustrated.

LIST OF REFERENCE NUMERALS

100 Urine work area
102 Urine work area manager
104 Urine test strip reader
106 Urine sediment analyzer
108 Interface between urine work area manager and urine test strip reader
110 Interface between urine work area manager and urine sediment analyzer
112 Hardware interface
114 Microprocessor
116 User interface
118 Display
120 Computer program product
122 Machine executable instructions
124 Expert system
300 Host
302 Network interface controlling urine work area
304 Result of command 302
306 Urine sample before urine test strip analysis
308 Urine sample before urine sediment analyzer analysis
310 Urine sample after both urine test strip analysis and urine sediment analysis
312 Interface controlling urine test strip reader and urine sediment analyzer
314 Result of urine test strip analysis
316 Result of urine sediment analysis
400 Graphical display of urine analysis
402 Region showing results of test strip analysis
404 Result showing result of urine sediment analysis
406 Result showing image acquired by urine sediment analyzer
408 Summary of urine sediment analysis for image 406
410 Graphical summary of urine sediment analysis for a series of 15 images
412 User interface for controlling display of urine sediment analysis results
414 User interface for closing graphical display of urine analysis
416 Horizontal axis
418 Vertical axis
420 Quantity of white blood cells
422 Selector
424 Button
426 Quantity of unclassified particles
428 Quantity of yeast
430 Quantity of white blood cells
500 Chemical or urine strip analysis results
502 Urine sediment analysis results
504 Uncritical results
506 Results which should be examined
600 Local user
602 Storage device
604 Firewall
606 Remote user
608 Healthcare IT environment (Laboratory information system)
610 Remote connection to factory
612 Remove connection to service representative
614 printer Aspects of the present invention may be embodied as a system, method or computer program product. Accordingly, aspects of the present invention may take the form of a hardware embodiment, a software embodiment or an embodiment combining software and hardware aspects. Furthermore, aspects of the present invention may take the form of a computer program product embodied in one or more computer readable storage medium(s) having computer readable program code embodied thereon, e.g., providing program code for use by or in connection with a computer or any instruction execution system.

Aspects of the present invention are described with reference to flowchart illustrations of methods, systems and computer program products. Each box of the flowchart illustrations can be implemented by computer program instructions. These computer program instructions may be provided to a processor such that the instructions, which execute via the processor of the computer or other programmable data processing apparatus, implement the functions of the flowchart boxes. In this regard, each block in the flowchart or block diagrams may represent a module, segment, or portion of code, which comprises one or more executable instructions for implementing the specified logical function(s).

Having thus described the invention of the present application in detail and by reference to embodiments thereof, it will be apparent that modifications and variations are possible without departing from the scope of the invention defined in the appended claims.

What is claimed is:

1. A urine work area manager for controlling a urine test strip reader and a urine sediment analyzer, wherein the urine work area manager comprises:
    a computing unit for executing machine executable instructions, wherein the computing unit transfers commands and data between the urine test strip reader and the urine work area manager using a first interface, and the computing unit transfers commands and data between the urine sediment analyzer and the urine work area manager using a second interface; and
    a set of machine executable instructions stored in a memory accessible by the computing unit that are executed by the computing unit for controlling the analysis of a plurality of urine samples, the computing unit executing the set of machine executable instructions to:
        instruct the urine test strip reader to analyze a select urine sample of the plurality of urine samples using the first interface;
        receive a strip analysis result from the urine test strip reader via the first interface;
        generate, based at least in part on the strip analysis result, a first set of instructions that indicate how the urine sediment analyzer should analyze the select sample of the plurality of urine samples by using the strip analysis result to project whether the urine sediment analyzer should dilute the select urine sample of the plurality of urine samples before instructing the urine sediment analyzer to analyze the select urine sample;
        instruct the urine sediment analyzer via the second interface with the first set of instructions to analyze the select urine sample, the set of machine executable instructions further comprising machine executable instructions to:
            determine from the strip analysis result from the urine test strip reader, a statistical threshold to be used with the urine sediment analyzer;
            receive a series of image analysis results from the urine sediment analyzer as each image analysis result is acquired; and
            stop the acquisition of further image analysis results where all image analysis results are within the statistical threshold, and
        receive a sediment analysis result from the urine sediment analyzer using the second interface;
        identify a sub-group of the plurality of urine samples for which the strip analysis result and the sediment analysis result disagree above a predetermined threshold;
        receive an instruction to re-analyze the urine samples identified as belonging to the sub-group after the plurality of samples have been analyzed; and
        instruct at least one of the urine sediment analyzer and the urine test strip reader to re-analyze each of the urine samples in the sub-group by identifying what analysis should be repeated.

2. The urine work area manager of claim 1, wherein the urine work area manager further comprises a display to display images, wherein the set of machine executable instructions further comprises instructions to:
    display at least one image acquired by the sediment analyzer for each urine sample in the sub-group;
    receive input from an operator for each urine sample in the sub-group indicating if the urine sample should remain in the sub-group or should be removed from the sub-group; and
    remove each urine sample from the sub-group that was indicated by the input before instructing the urine sediment analyzer to reanalyze urine samples in the sub-group.

3. The urine work area manager of claim 1, wherein:
    the machine executable instructions to stop the acquisition of further image analysis results further comprises machine executable instructions to stop the acquisition where all image analysis results are within the statistical threshold and the analysis results agree with the result of the urine test strip reader, and further comprising:
    the set of machine executable instructions further comprises machine executable instructions to continue the acquisition of further image analysis results where all image analysis results are within a statistical threshold and the analysis results disagree with the result of the urine test strip reader.

4. The urine work area manager of claim 1, wherein the set of the machine executable instructions further comprises machine executable instructions to:
    receive an instruction to analyze the urine sample in a research mode;
    instruct the urine sediment analyzer to acquire a series of image analysis results for the urine sample using a first predetermined number of images, wherein the first predetermined number of images is larger than a number of images collected during a normal operation; and
    analyze the acquired series of images to obtain statistics of the urine sediments.

5. The urine work area manager of claim 1, wherein the urine work area manager further comprises a display, wherein the urine work area manager further comprises a graphical user interface that receives user input, wherein the set of machine executable instructions further comprises machine executable instructions to:
    display a summary of the strip analysis result and the sediment analysis result on the display; and
    perform at least one of receiving an input from the operator indicating approval or disapproval of the strip analysis result and the sediment analysis result for each urine sample, editing a comment and appending a comment, wherein urine analysis results that are not approved are placed into the sub-group.

6. The urine work area manager of claim 1, wherein the urine test strip reader comprises a needle for dispensing urine during operation, wherein the set of machine executable instructions further comprises machine executable instructions to:
    determine whether the needle of the urine test strip reader should be cleaned based on results of the urine test strip reader;
    instruct the urine test strip reader via the first interface to wash the needle if the determination concludes that the needle should be washed; and
    reanalyze at least one sample in the sub-group.

7. The urine work area manager of claim 1, wherein the urine work area manager further comprises a display, wherein the set of machine executable instructions further comprises machine executable instructions to graphically display which of the plurality of urine samples are a member of the sub-group before instructing the urine sediment analyzer to reanalyze the urine samples that are a member of the sub-group, wherein a graphical user interface enables a user to manually remove members of the sub-group, add new members to the sub-group, and sort the sub-group.

8. The urine work area manager of claim 1, wherein the urine work area manager further comprises a display, wherein the urine work area manager receives a sediment analysis result which comprises at least two images, wherein the set of machine executable instructions further comprises machine executable instructions to graphically display the relative numbers of different types of sediments in each of the at least two images.

9. The urine work area manager of claim 1, wherein the urine work area manager further comprises a display, wherein set of the machine executable instructions further comprises machine executable instructions to graphically display a summary of the strip analysis result and the sediment analysis result, wherein the strip analysis result comprises at least one chemical analysis and the sediment analysis identifies the quantity of at least one type of particulate, and wherein the summary shows the at least one chemical analysis and the quantity of at least one type of particulate using normalized graphs.

10. The urine work area manager of claim 1, wherein the urine work area manager further comprises a display, wherein the urine work area manager further comprises a microscope selector, wherein the set of machine executable instructions further comprises machine executable instructions to activate a microscope control interface when the microscope selector is selected, wherein the microscope control interface receives user input and generates microscope control instructions which are sent to the urine sediment analyzer via the second interface, and wherein the display is utilized to display microscope images received via the second interface from the sediment analyzer.

11. The urine work area manager of claim 10, wherein the set of machine executable instructions further comprises machine executable instructions to output a signal whenever any one of the following occurs: the urine sediment analysis result contains more than a second predetermined number of unclassified particles, the urine sediment analysis result contains more than a third predetermined number of particles, the urine work area manager is being operated in a research mode.

12. The urine work area manager of claim 1, wherein the urine work area manager is located within the same housing as the urine sediment analyzer, wherein the urine work area manager and the urine sediment analyzer are operated using the same computing unit, and wherein the second interface is implemented in software.

13. The urine work area manager of claim 1, the set of machine executable instructions further comprising machine executable instructions stored in a memory accessible by the computing unit that are executed by the computing unit to:
combine the strip analysis result with the sediment analysis result into a combined result for every sample;
compare the strip analysis result with the sediment analysis result; and
validate the combined result when there is no disagreement between the strip analysis result and the sediment analysis result.

14. The urine work area manager of claim 1, the set of machine executable instructions further comprising machine executable instructions stored in a memory accessible by the computing unit that are executed by the computing unit to:
determine that the strip analysis result and the sediment analysis result disagree based upon at least one of: an error in performing one of the tests, and a difference due to the age of the urine sample.

15. The urine work area manager of claim 1, the set of machine executable instructions further comprising machine executable instructions stored in a memory accessible by the computing unit that are executed by the computing unit to:
implement a graphical user interface that receives interaction from an operator to manually modify the sub-group before executing the set of machine executable instructions to re-analyze the urine samples identified as belonging to the sub-group.

16. The urine work area manager of claim 15, wherein:
the machine executable instructions to implement a graphical user interface that receives interaction from an operator comprises machine executable instructions to receive a select interaction from the operator to manually modify the sub-group by identifying samples added to the sub-group.

17. The urine work area manager of claim 15, wherein:
the machine executable instructions to implement a graphical user interface that receives interaction from an operator comprises machine executable instructions to receive a select interaction from the operator to manually modify the sub-group by manually removing samples from the sub-group.

18. The urine work area manager of claim 1, wherein the machine executable instructions to use the strip analysis result to project whether the urine sediment analyzer should dilute a select urine sample of the plurality of urine samples before instructing the urine sediment analyzer to analyze the plurality of urine samples, comprises machine executable instructions to:
check the strip analysis result to determine if each of the plurality of urine samples meets a first predetermined condition; condition, wherein the first predetermined condition is selected from: the leukocyte concentration is 3+, the erythrocyte concentration is 4+, the nitrite level is positive, and both the leukocyte concentration is 2+ and the erythrocyte concentration is 3+; and
generate instructions for the urine sediment analyzer to dilute each urine sample that meets the first predetermined condition.

19. The urine work area manager of claim 1, wherein the urine work area manager further comprises a display and a selector, wherein:
the urine work area manager receives a sediment analysis result which comprises at least two images, where the set of machine executable instructions further comprises machine executable instructions to graphically display indicia of different types of sediments in each of the at least two images; and
the selector allows an operator to select images based on the relative numbers of different types of particulates.

20. The urine work area manager of claim 1, wherein the set of machine executable instructions further comprises machine executable instructions to:
instruct a user to manually re-load into at least one of the urine test strip reader and a urine sediment analyzer, samples of the sub-group for re-testing.

21. The urine work area manager of claim 1, the set of machine executable instructions further comprising machine executable instructions to:
place the samples of the sub-group to be re-tested by the urine sediment analyzer into an input buffer of the urine sediment analyzer; and
check sample identification and rack identification of each sample placed back into the input buffer.

22. A urine work area manager for controlling a urine test strip reader and a urine sediment analyzer, wherein the urine work area manager comprises:
a computing unit for executing machine executable instructions, wherein the computing unit transfers commands and data between the urine test strip reader and the urine work area manager using a first interface, and the computing unit transfers commands and data between the urine sediment analyzer and the urine work area manager using a second interface; and
a set of machine executable instructions stored in a memory accessible by the computing unit that are executed by the computing unit for controlling the analysis of a plurality of urine samples, the computing unit executing the set of computer executable instructions to:
instruct the urine test strip reader to analyze a select urine sample of the plurality of urine samples using the first interface;
receive a strip analysis result from the urine test strip reader via the first interface;
generate, based at least in part on the strip analysis result, a first set of instructions that indicate how the urine sediment analyzer should analyze the select sample of the plurality of urine samples by using the strip analysis result to project whether the urine sediment analyzer should dilute the select urine sample of the plurality of urine samples before instructing the urine sediment analyzer to analyze the select urine sample;
instruct the urine sediment analyzer via the second interface with the first set of instructions to analyze the select urine sample;
receive a sediment analysis result from the urine sediment analyzer using the second interface;
identify a sub-group of the plurality of urine samples for which the strip analysis result and the sediment analysis result disagree above a predetermined threshold;
receive an instruction to re-analyze the urine samples identified as belonging to the sub-group after the plurality of samples have been analyzed; and
instruct at least one of the urine sediment analyzer and the urine test strip reader to re-analyze each of the urine samples in the sub-group by identifying what analysis should be repeated;
wherein:
the set of machine executable instructions to the urine sediment analyzer and/or the urine test strip reader to re-analyze urine samples in the sub-group further comprises machine executable instructions to:
decide to re-run the urine sediment analyzer with manual investigation;
define sample number and test parameters that are to be measured again;
place the urine samples that are to be measure again into an input buffer of the urine sediment analyzer;
change, automatically, by the urine sediment analyzer, into a microscope mode as soon as a sample to be re-tested has been pipetted into a cuvette and has been centrifuged so as to be ready for the manual investigation;
collect at least one image taken by an operator;
return a list of particulate types and numbers based upon an analysis of the at least one image taken by the operator; and
attach the list to an associated sample record.

\* \* \* \* \*

UNITED STATES PATENT AND TRADEMARK OFFICE
CERTIFICATE OF CORRECTION

| | |
|---|---|
| PATENT NO. | : 9,443,058 B2 |
| APPLICATION NO. | : 12/841445 |
| DATED | : September 13, 2016 |
| INVENTOR(S) | : Mark Busenhart et al. |

It is certified that error appears in the above-identified patent and that said Letters Patent is hereby corrected as shown below:

In the Claims

1 – Claim 3, Column 18, Lines 22-23, "further comprising" should be deleted;

2 – Claim 9, Column 19, Line 21, "wherein set of the machine" should read --wherein the set of machine--;

3 – Claim 19, Column 20, Line 55, "where the" should read --wherein the--; and

4 – Claim 22, Column 21, Line 23, "the set of computer executable" should read --the set of machine executable--.

Signed and Sealed this
Twenty-eighth Day of March, 2017

Michelle K. Lee
*Director of the United States Patent and Trademark Office*